(12) United States Patent
Kankan et al.

(10) Patent No.: US 7,439,367 B2
(45) Date of Patent: Oct. 21, 2008

(54) PHARMACEUTICAL PROCESS AND COMPOUNDS PREPARED THEREBY

(75) Inventors: Rajendra Narayanrao Kankan, Maharashtra (IN); Dharmaraj Ramachandra Rao, Maharashtra (IN); Pathi L. Srinivas, Karnataka (IN)

(73) Assignee: CIPLA Limited, Mumbai Central (IN)

( * ) Notice: Subject to any disclaimer, the term of this patent is extended or adjusted under 35 U.S.C. 154(b) by 0 days.

(21) Appl. No.: 10/542,268

(22) PCT Filed: Jan. 12, 2004

(86) PCT No.: PCT/GB2004/000064

§ 371 (c)(1),
(2), (4) Date: Jan. 5, 2006

(87) PCT Pub. No.: WO2004/063188

PCT Pub. Date: Jul. 29, 2004

(65) Prior Publication Data

US 2006/0205791 A1    Sep. 14, 2006

(30) Foreign Application Priority Data

Jan. 15, 2003  (IN) .......................... 58MUM2003
Feb. 14, 2003  (IN) .......................... 193MUM2003

(51) Int. Cl.
*C07D 401/12* (2006.01)
(52) U.S. Cl. .................................. 546/273.7
(58) Field of Classification Search ............... 546/273.7
See application file for complete search history.

(56) References Cited

U.S. PATENT DOCUMENTS 4,555,518 A * 11/1985 Rainer ...................... 514/338
4,758,579 A * 7/1988 Kohl et al. ................. 514/338
6,107,312 A   8/2000 Kohl et al.

FOREIGN PATENT DOCUMENTS

RU         2142459         12/1999

OTHER PUBLICATIONS

Vippagunta et al., "Crystalline Solids", Advanced Drug Delivery Reviews 48 (2001) 3-26.*
Guillory, "Generation of Polymorphs, etc.," in Brittain ed., Polymorphism, etc., NY: Marcel Dekker, Inc., 1999, 183-226.*
Vyas L et al: "Lansoprazole, An Antiulcerative Drug": ACTA Crystalographica Section C. Crystal Structure Communications, Munksgaard, Copenhagen, DK, vol. C56, No. 12, 2000, pp. E572-E573, XP009014904.
Graul A. et al. "Esomeprazole Magnesium (-)-Omeprazole Magnesium Perprazole (Formerly) (S)- Omeprazole Magnesium H-199/18 Nexium"; Drugs of the Fugure, Barcelona, ES, vol. 24, No. 11, 1999, pp. 1178-1183, XP009026689.
Williams M P et al: "Review article: the pharmacology of rabeprazole"; Alimentary Pharmacology & Therapeutics, Blackwell Scientific Publications Ltd., Cambridge, GB, vol. 13, No. 3, 1999, pp. 3-10, XP002963613.
Garner A. et al: "Pantoprazole: A new and More Specific Proton Pump Inhibitor"; Expert Opinion on Investigational Drugs, Ashley Publication Ltd., London, GB, vol. 6, No. 7, 1997, pp. 885-893, XP009025982.

* cited by examiner

*Primary Examiner*—Patricia L Morris
(74) *Attorney, Agent, or Firm*—Novak Druce + Quigg LLP

(57) ABSTRACT

The present invention relates to an improved process for the preparation of a sulfinyl compound of formula (I), or a pharmaceutically acceptable salt, hydrate or solvate thereof, from a sulfide compound of formula (II), wherein in both formulae (I) and (II) $R_1$ and $R_3$ are selected from the group consisting of hydrogen, methyl or $C_{1-4}$ alkoxy, $R_2$ is selected from the group consisting of substituted or unsubstituted $C_{1-4}$ alkoxy and $R_4$ is selected from the group consisting of hydrogen or substituted or unsubstituted $C_{1-4}$ alkoxy.

12 Claims, No Drawings

PHARMACEUTICAL PROCESS AND COMPOUNDS PREPARED THEREBY

This application is a 35 U.S.C. §371 U.S. National Stage Application of International Application No. PCT/GB2004/000064, filed on Jan. 12, 2004, claiming the priority of Indian Application No. 58/MUM/2003, filed Jan. 15, 2003 and Indian Application No. 193/MUM/2003, filed Feb. 14, 2003, the entire disclosures of which are incorporated herein by reference in their entireties.

The present invention relates to an improved process for preparation of proton pump inhibitors, and to such proton pump inhibitors prepared thereby, compositions containing the same and uses thereof Gastric proton pump inhibitors (PPIs) include substituted 2-(2-pyridylmethyl)-sulfinyl-1H-benzimidazoles, such as lansoprazole (2-[[[3-methyl-4-(2,2,2-trifluoro-ethoxy)-2-pyridinyl]methyl]sulfinyl]1H-benzimidazole), omeprazole (5-methoxy-2-[[(4methoxy-3,5-dimethyl-2-pyirdyl)methyl]sulfinyl]-1H-benzimidazole), pantoprazole (5-(difluoromethoxy)-2-[[(3,4-dimethoxy-2-pyridinyl)methyl]sulfinyl]1H-benzimidazole) and rabeprazole (2-[[[4-(3-methoxypropoxy)3-methyl-2-pyridinyl]methyl]sulfinyl]-1H-benzimidazole). These compounds can produce profound and sustained inhibition of gastric acid secretion, with responses of PPIs being more rapid compared with those seen with other anti-secretory drugs. PPIs work by inhibiting the production of stomach acid, by shutting down a system in the stomach known as proton pump, the full name of which is the hydrogen-potassium adenosine triphosphate enzyme system. PPIs are the drugs of choice in dyspepsia and peptic ulcers, and also Zollinger-Ellyson syndrome. In particular, in the treatment of peptic ulcers, the response rates of PPIs are superior to those seen with other drugs.

The reported prior art synthesis of these substituted 2-(2-pyridylmethyl)-sulfinyl-1H-benzimidazoles generally involves an oxidation process of a sulfide compound to the corresponding sulfinyl compound. More particularly, prior art processes for the preparation of 2-2-pyridylmethyl)-sulfinyl-1H-benzimidazoles, generally involve the synthesis of the corresponding thioether compound, and its subsequent oxidation to the sulfinyl or sulfoxy compound, by various methods such as reaction with hydrogen peroxide over a vanadium compound catalyst, or reaction with peracids, peresters or ozone. There are several disadvantages associated with such known processes, primarily with respect to the nature of the thioether (or sulfide) compound being oxidized.

U.S. Pat. No. 4,628,098 to Nohara, et al. discloses a process for preparation of lansoprazole by oxidation of the sulphide precursor compound using peracids (m-chloro perbenzoic acid).

U.S. Pat. No. 5,840,552 to Holt, et al. discloses a process for preparation of lansoprazole, wherein the sulphide precursor compound was selectively bio-oxidised to isolate the pharmaceutically active enantiomer or enantiomerically enriched corresponding sulfoxide form, using microorganisms or a microbial enzyme system.

U.S. Pat. No. 5,374,730, to Slemon, et al. discloses a process for the preparation of omeprazole and lansoprazole, wherein amide analogues of the thioether compounds were readily oxidized to the corresponding sulfinyl compounds and the sulfinyl compounds were hydrolyzed in an alkaline medium to the corresponding carboxylic acid salts. The salts were subsequently decarboxylated to omeprazole or lansoprazole respectively. The disclosure refers to the advantages in relation to the purity of the final products, and the simplicity of the purification procedures. The amide compounds which were subjected to the oxidation step were crystalline solids, as opposed to oils, and as such could be readily purified to a high degree of purity by relatively simple precipitation, crystallization and washing procedures. The carboxylates and carboxylic acid salts which were formed in the subsequent synthetic step after oxidation were water soluble, whereas the final products, omeprazole and lansoprazole, are not water soluble. Accordingly, any un-reacted residues, and also other minor impurities in the final products, were simply removable by an aqueous washing procedure. Avoidance of significant discoloration of the product was the other advantage disclosed.

U.S. Pat. No. 5,470,983 to Slemon, et al. discloses processes for producing lansoprazole from acetamide-sulfide compounds by a process of oxidation to form the amide sulfinyl compound, followed by alkaline hydrolysis to the sulfinyl carboxylate or salt, and decarboxylation.

U.S. Pat. No. 5,502,195, to Slemon, et al. discloses a process for preparation of lansoprazole, wherein the acetamide sulphide was oxidized to the corresponding amide sulfinyl compound, which was subsequently hydrolysed in an alkaline medium to the carboxylic acid salt and then decarboxylated to form lansoprazole.

U.S. Pat. No. 6,423,846 to Moon, et al. discusses problems associated with prior art oxidation procedures for converting precursor compounds into lansoprazole, where many by products were formed and the yield of lansoprazole was low. EP Patent No. 134,400, GB Patent No. 2,134,523, U.S. Pat. No. 4,628,098 and Korean Patent No. 52,837 each disclose m-chloroperbenzoic acid as the oxidant. Spanish Patent Nos. 550,057; 540,147 and 539,793 respectively disclose sodium periodate, iodosomethylbenzene and iodosobenzene as the oxidant employed. These prior art processes were cited as being unviable because of the expensive oxidants used therein, the formation of many impurities and a low yield of the product in the range of about 60 to 80%.

All these prior art process either use expensive catalysts or hazardous oxidizing reagents, such as peracids, which are not suitable for commercial manufacture of these compounds. Also over-oxidation of the thioether compound to the corresponding sulphone analogue is a common problem encountered with the prior art processes.

There has thus been a long felt need for efficient and safe methods for the selective oxidation of a sulphide compound of formula (II)

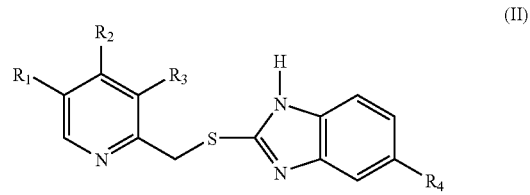

to a sulfinyl compound of formula (I)

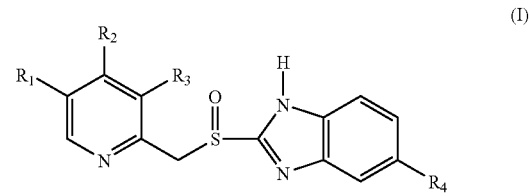

wherein in both formulae (I) and (II) $R_1$ and $R_3$ are selected from the group consisting of hydrogen, methyl or $C_{1-4}$alkoxy, $R_2$ is selected from the group consisting of substituted or unsubstituted $C_{1-4}$alkoxy and $R_4$ is selected from the group consisting of hydrogen or substituted or unsubstituted $C_{1-4}$alkoxy.

The present invention now provides an efficient, safe and industrially feasible method for preparing various substituted 2-(2-pyridylmethyl)-sulfinyl-1H-benzimidazoles.

In particular, it is an aim of the present invention to provide an improved process for oxidation of (2-[[[3-methyl-4-(2,2, 2-trifluoro-ethoxy)-2-pyridinyl]methyl]thio]1H-benzimidazole to the corresponding (2-[[[3-methyl-4-(2,2,2-trifluoroethoxy)-2-pyridinyl]methyl]-sulfinyl]1H-benzimidazole (lansoprazole), preferably using an eco-friendly, inexpensive and readily available reagent.

It is a further aim of the present invention is to provide an improved process for oxidation of ((5-methoxy-2-[[(4-methoxy-3,5-dimethyl-2-pyirdyl)methyl]-thio]-1H-benzimidazole, to the corresponding ((5-methoxy-2-[[(4-methoxy-3,5-dimethyl-2-pyirdyl)methyl]-sulfinyl]-1H-benzimidazole (omeprazole), preferably using an eco-friendly, inexpensive and readily available reagent.

It is a further aim of the present invention is to provide an improved process for oxidation of ((5-(difluoromethoxy)-2-[[(3,4-dimethoxy-2-pyridinyl)methyl]thio]1H-benzimidazole, to the corresponding ((5-difluoromethoxy)-2-[[(3,4-dimethoxy-2-pyridinyl)methyl]-sulfinyl]1H-benzimidazole (pantoprazole), preferably using an eco-friendly, inexpensive and readily available reagent.

It is a still further aim of the present invention is to provide an improved process for oxidation of (2-[[[4-(3-methoxy-propoxy)3-methyl-2-pyridinyl]methyl]-thio]-1H-benzimidazole, to the corresponding (2-[[[4-(3-methoxy-propoxy)3-methyl-2-pyridinyl]methyl]-sulfinyl]-1H-benzimidazole (rabeprazole), preferably using an eco-friendly, inexpensive and readily available reagent.

More particularly, the present invention provides a process for preparing a sulfinyl compound of formula (I), or a pharmaceutically acceptable salt, hydrate or solvate thereof,

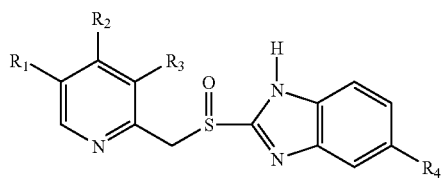
(I)

which process comprises oxidation of a sulfide compound of formula (II)

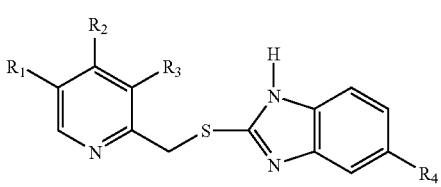
(II)

wherein in both formulae (I) and (II) $R_1$ and $R_3$ are selected from the group consisting of hydrogen, methyl or $C_{1-4}$alkoxy, $R_2$ is selected from the group consisting of substituted or unsubstituted $C_{1-4}$alkoxy and $R_4$ is selected from the group consisting of hydrogen or substituted or unsubstituted $C_{1-4}$alkoxy;

wherein a compound of formula (II) is added to a solvent, or a mixture of solvents, to form a reaction mixture, an oxidizing agent is added to said reaction mixture and said oxidation is carried out at a controlled temperature and pH so as to prepare a compound of formula (I), and optionally converting a sulfinyl compound of formula (I) to a pharmaceutically acceptable salt, hydrate or solvate thereof;

characterised in that an alkali is present in the reaction mixture at least during said oxidation, whereby the pH of the reaction mixture at least during said oxidation is in the range of 9 to 12. Preferably the oxidizing agent comprises an aqueous hypohalite solution.

The present invention further provides a process for preparing a sulfinyl compound of formula (I), or a pharmaceutically acceptable salt hydrate or solvate thereof,

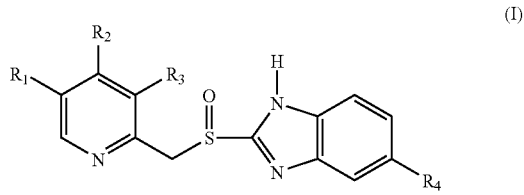
(I)

which process comprises oxidation of a sulfide compound of formula (I)

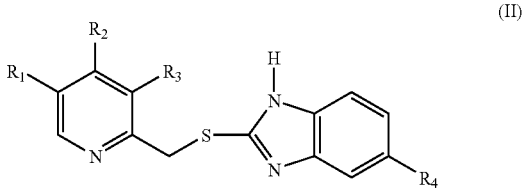
(II)

wherein in both fornulae (I) and (II) $R_1$ and $R_3$ are selected from the group consisting of hydrogen, methyl or $C_{1-4}$alkoxy, $R_2$ is selected from the group consisting of substituted or unsubstituted $C_{1-4}$alkoxy and $R_4$ is selected from the group consisting of hydrogen or substituted or unsubstituted $C_{1-4}$alkoxy;

characterised in that said compound of formula (II) is reacted with an oxidizing agent comprising an aqueous hypohalite solution, and optionally converting a sulfinyl compound of formula (I) to a suitable pharmaceutically acceptable salt, hydrate or solvate thereof Optionally, a compound of formula (II) is reacted with an aqueous hypohalite solution in the presence of a catalyst, suitably selected from the group consisting of pyridine, di-isopropyl ethyl amine and N,N-dimethyl amino pyridine. The use of such a catalyst is desirable to further avoid formation of undesirable by products.

Typically, a process according to the present invention comprises dissolving or suspending a sulphide precursor compound of formula (II) in a suitable solvent or mixture of solvents. Suitably, the solvent comprises water, lower alkyl alcohols, esters, ethers, chlorinated solvents, or mixtures thereof. A preferred solvent is selected from the group consisting of water, methanol, ethanol, isopropanol, di-isopropyl ether, dichloromethane, acetonitrile and ethyl acetate, or a mixture of two or more of these solvents. An aqueous hypohalite solution, preferably sodium hypochlorite, is then added slowly in a controlled manner at appropriate temperature conditions to give, after simple work up procedures, a sulfinyl compound of formula (I) in very high yield and purity.

A process according to the present invention is typically performed at a temperature in the range of −30 to 50° C. A preferred operating temperature is in the range of 0 to 30° C.

An aqueous hypohalite solution suitable for use in a process according to the present invention typically comprises an aqueous solution of an alkali metal or alkali earth metal hypohalite and is preferably selected from the group consisting of sodium hypochlorite, sodium hypochlorite and calcium hypochlorite. Sodium hypochlorite is most preferred. An aqueous hypohalite solution suitable for use in a process according to the present invention typically has a concentration in the range of 2% to 30%. It is preferable, however, to use an aqueous hypohalite solution having a concentration in the range of 2% to 5%, for ease of handling.

The aqueous hypohalite solution is typically added to a reaction mixture comprising a sulphide precursor compound of formula (II) dissolved or suspended in a suitable solvent, or mixture of solvents, over a time period ranging from several minutes to several hours, depending on the strength of the hypohalite solution and the exothermicity of the reaction. It is preferable to perform the addition slowly over a period ranging from 30 minutes to 4 hours, with the time taken for completion of the reaction ranging from 2 to 10 hours.

A commercially available hypohalite solution can be employed, but it is advantageous to use a freshly prepared solution typically including about 0.5% to 5% of free corresponding alkali or alkali earth metal hydroxide. The presence of free alkali or alkali earth metal hydroxide not only stabilizes the hypohalite, but also exhibits an advantageous stabilising effect on the benzimidazole sulphinyl products which are known to be unstable in acidic conditions. Alternatively, a solution of an alkali or alkali earth metal hydroxide, or other suitable alkali, can be added to the suspension or solution of a precursor sulphide compound of formula (II) in the solvent, or mixture of solvents, before addition of the oxidizing agent.

A sulfinyl compound of formula (I) can be suitably isolated from the reaction mass by adjusting the pH using aqueous organic or inorganic acids. Typically, the pH is adjusted to be in the range of 6.0 to 9.5, more preferably in the range of 7 to 7.5, using aqueous acetic acid, followed by filtration to isolate a sulfinyl compound of formula (I).

A sulfinyl compound of formula (I) may be further purified by dissolving in a mixture of a $C_{1-4}$ alkanol, typically methanol, and an aqueous alkali metal hydroxide solution, typically sodium hydroxide solution. The pH of the resulting clear solution is adjusted to between 9.0 to 9.5, typically using aqueous ammonium acetate solution, and a sulfinyl compound of formula (I) is isolated by filtration.

Substantially as hereinbefore described a process according to the present invention can further comprise conversion of a sulfinyl compound of formula (I) to a suitable pharmaceutically acceptable salt, hydrate or solvate thereof, in particular a pharmaceutically acceptable salt form. Suitable salts include those with alkali or alkali earth metals, for example $Mg^{2+}$, $Ca^{2+}$, $Na^+$, $K^+$ or $Li^+$ salts, in particular $Mg^{2+}$ or $Na^+$ salts.

In the case where $R_2$ represents substituted alkoxy substantially as hereinbefore described, suitable substituents include one or more halo substituents, such as one or more fluoro substituents, or one or more alkoxy substituents, such as $C_{1-3}$ alkoxy, especially methoxy.

In the case where $R_4$ represents substituted alkoxy substantially as hereinbefore described, suitable substituents include one or more halo substituents, such as one or more fluoro substituents.

A preferred compound prepared according to a process of the present invention is lansoprazole, wherein in formula (I) $R_1$ represents methyl $R_2$ represents trifluoroethoxy, $R_3$ represents hydrogen and $R_4$ represents hydrogen A further preferred compound prepared according to a process of the present invention is omeprazole, wherein in formula (I) $R_1$ represents methyl, $R_2$ represents methoxy, $R_3$ represents methyl and $R_4$ represents methoxy.

A further preferred compound prepared according to a process of the present invention is pantoprazole, wherein in formula (I) $R_1$ represents methoxy, $R_2$ represents methoxy, $R_3$ represents hydrogen and $R_4$ represents difluoromethoxy.

A further preferred compound prepared according to a process of the present invention is rabeprazole, wherein in formula (I) $R_1$ represents methyl, $R_2$ represents $OCH_2CH_2CH_2OMe$, $R_3$ represents hydrogen and $R_4$ represents hydrogen.

The present invention further provides lansoprazole prepared by a process substantially as hereinbefore described. Preferably lansoprazole thus provided by the present invention is substantially free of oxidation contamination by products.

The present invention further provides omeprazole prepared by a process substantially as hereinbefore described. Preferably omeprazole thus provided by the present invention is substantially free of oxidation contamination by products.

The present invention further provides pantoprazole prepared by a process substantially as hereinbefore described. Preferably pantoprazole thus provided by the present invention is substantially free of oxidation contamination by products.

The present invention further provides rabeprazole prepared by a process substantially as hereinbefore described. Preferably rabeprazole thus provided by the present invention is substantially free of oxidation contamination by products.

The present invention further provides a pharmaceutical composition comprising a sulfinyl compound of formula (I)

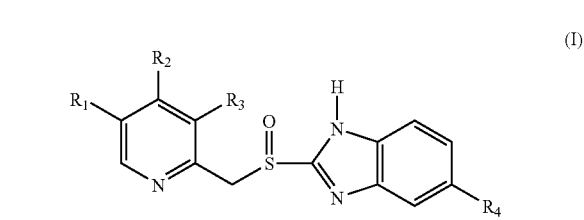

(I)

wherein $R_1$ and $R_3$ are selected from the group consisting of hydrogen, methyl or $C_{1-4}$alkoxy, $R_2$ is selected from the group consisting of substituted or unsubstituted $C_{1-4}$alkoxy and $R_4$ is selected from the group consisting of hydrogen or substituted or unsubstituted $C_{1-4}$alkoxy; which compound of formula (I) is prepared by a process substantially as hereinbefore described; together with a pharmaceutically acceptable carrier or excipient therefore. A preferred composition according to the present invention comprises lansoprazole prepared by a process substantially as hereinbefore described; together with a pharmaceutically acceptable carrier or excipient therefore. A further preferred composition according to the present invention comprises omeprazole prepared by a process substantially as hereinbefore described; together with a pharmaceutically acceptable carrier or excipient therefore. A further preferred composition according to the present invention comprises pantoprazole prepared by a process substantially as hereinbefore described; together with a pharmaceutically acceptable carrier or excipient therefore. A still further preferred composition according to the present invention comprises rabeprazole prepared by a process substantially as hereinbefore described; together with a pharmaceutically acceptable carrier or excipient therefore.

There is further provided by the present invention, for use in therapy, lansoprazole prepared by a process substantially as hereinbefore described. There is also provided, for use in therapy, omeprazole prepared by a process substantially as hereinbefore described. There is also provided for use in therapy, pantoprazole prepared by a process substantially as hereinbefore described. There is still further provided for use in therapy, rabeprazole prepared by a process substantially as hereinbefore described.

The present invention also provides for use in the manufacture of a medicament for the treatment of gastric ulcers and related conditions, lansoprazole prepared by a process substantially as hereinbefore described. There is also provided for use in the manufacture of a medicament for the treatment of gastric ulcers and related conditions, omeprazole prepared by a process substantially as hereinbefore described. There is also provided for use in the manufacture of a medicament for the treatment of gastric ulcers and related conditions, pantoprazole prepared by a process substantially as hereinbefore described. There is still further provided for use in the manufacture of a medicament for the treatment of gastric ulcers and related conditions, rabeprazole prepared by a process substantially as hereinbefore described.

The present invention also provides a method of treating gastric ulcers and related conditions, which comprises administering to a patient in need of such treatment lansoprazole prepared by a process substantially as hereinbefore described. The present invention also provides a method of treating gastric ulcers and related conditions, which comprises administering to a patient in need of such treatment omeprazole prepared by a process substantially as hereinbefore described. The present invention also provides a method of treating gastric ulcers and related conditions, which comprises administering to a patient in need of such treatment pantoprazole prepared by a process substantially as hereinbefore described. The present invention also provides a method of treating gastric ulcers and related conditions, which comprises administering to a patient in need of such treatment rabeprazole prepared by a process substantially as hereinbefore described.

The present invention is now further illustrated by the following examples, which do not in any way limit the scope of the invention. While the present invention is described above in connection with preferred or illustrative embodiments, these embodiments are not intended to be exhaustive or limiting of the invention. Rather, the invention is intended to cover all alternatives, modifications and equivalents included within its scope, as defined by the appended claims.

EXAMPLES

Example 1

Preparation of 2-[[[4-(3-methoxy-propoxy)-3-methyl-2-pyridinyl] methyl]-sulfinyl]-1-H-benzimidazole sodium (rabeprazole sodium)

2-[[[4-(3-methoxy-propoxy)-3-methyl-2-pyridinyl]methyl]-thio]-1H-benzimidazole (10 g) was suspended in 200 ml of purified water, sodium hydroxide (about 2 g) and pyridine (4 ml). To this was slowly added about 75 g of approximately 3.8% sodium hypochlorite solution in 2 hours. The reaction mass was maintained at 5-8° C. for 4 hours. After completion of the reaction, excess sodium hypochlorite was decomposed using 5% aqueous sodium thiosulphate solution. The pH was adjusted to between 8.0 to 9.0 using 10% ammonium acetate solution.

After pH adjustment the compound was isolated from the water layer by adding ethyl acetate followed by extraction. Concentrating the organic layer under vacuum yielded a residue to which isopropyl acetate was added and stirred for about 1 hour, yielding the desired product. The product was purified by dissolving in a mixture of acetone and triethylamine. Rabeprazole base so obtained was dissolved in ethyl acetate and methanolic ammonia mixture to which methanolic sodium hydroxide was added and distilled off to a thick residue at low temperature. This was again redissolve in ethyl acetate and rabeprazole sodium salt was isolated in n-heptane/n-hexane and dried.

Example 2

Preparation of 5-(difluoromethoxy)-2-[[[(3,4-dimethoxy-2-pyridinyl)methyl] sulfinyl]-1H-benzimidazole (pantoprazole)

5-(difluoromethoxy)-2-[[(3,4-dimethoxy-2-pyridinyl)methyl]-thio]-1H-benzimidazole (10 g) was dissolved in purified water (100 ml) and methanol (10 ml). 80 g of 3.5% aqueous sodium hypochlorite solution having a sodium hydroxide content of up to 2.4-2.8% was added to the reaction mass, which was maintained at 5-8° C. for about 1 hour. Excess hypochlorite was decomposed using 5% aqueous sodium thiosulphate solution. pH of the reaction mass was adjusted to 8.0-9.5 using ammonium acetate. The solids were filtered, washed with chilled water and dried in an oven to give 8.5 g of the title compound.

Example 3

Preparation of (2-[[[3-methyl-4-(2,2,2-trifluoro-ethoxy)-2-pyridinyl]methyl]-sulfinyl]1H-benzimidazole (lansoprazole)

(2-[[[3-methyl-4-(2,2,2-trifluoro-ethoxy)-2-pyridinyl] methyl]-thio]1H-benzimidazole (10 g) was suspended in 100 ml of a mixture of acetonitrile and water (7:3). A solution of sodium hydroxide was added to this suspension. 61 g of sodium hypochlorite solution (4.2%) was added over a period of 4 hours maintaining a temperature of 5° C.-10° C. Excess hypochlorite was decomposed using 3% aqueous sodium metabisulfite solution. Acetone (50 ml) was added and the pH was adjusted to between 7.5 to 8.5 using dilute acetic acid. The solids were filtered, washed with chilled water and dried in an oven to give 8 g of the title compound. The product was slurried in acetone followed by purification by dissolving in a mixture of acetone and aqueous sodium hydroxide solution.

The pH of the clear solution was adjusted to about 7.0-8.0 using dilute acetic acid solution and the product was isolated by filtration, slurried in water and dried in an oven to give about 7 g of the desired product.

Example 4

Preparation of ((5-methoxy-2-[[4-methoxy-3,5-dimethyl-2-pyirdyl)methyl]sulfinyl]-1H-benzimidazole (omeprazole)

((5-methoxy-2-[[(4-methoxy-3,5-dimethyl-2-pyirdyl)methyl]-thio]-1H-benzimidazole, (20 g) was suspended in 200 ml of dichloromethane. 140 g of sodium hypochlorite solution (chlorine content: 3.6-4.2%; sodium hydroxide content: 2.8-3.0%) was added over a period of 3 hours maintaining a temperature of −5° C. to 0° C. The organic layer was separated and extracted with 200 ml of 5% sodium hydroxide solution. The pH of the aqueous layer was adjusted to between 8-8.5 using dilute acetic acid. The solids were filtered, washed with chilled water and dried in an oven to give 17 g of the title compound.

The invention claimed is:

1. A process for preparing a sulfinyl compound of formula (I), or a pharmaceutically acceptable salt thereof,

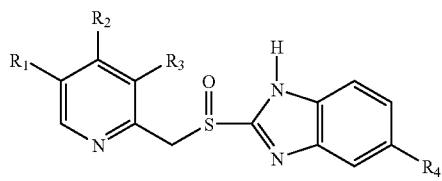
(I)

which process comprises oxidation of a sulfide compound of formula (II)

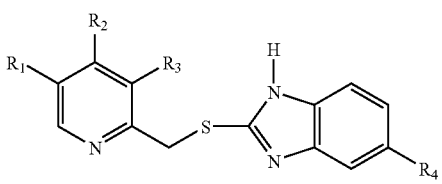
(II)

wherein in both formulae (I) and (II) $R_1$ and $R_3$ are selected from the group consisting of hydrogen, methyl or $C_{1-4}$alkoxy, $R_2$ is selected from the group consisting of substituted or unsubstituted $C_{1-4}$alkoxy and $R_4$ is selected from the group consisting of hydrogen or substituted or unsubstituted $C_{1-4}$ alkoxy;

characterized in that an oxidizing agent comprising an aqueous alkali or alkali earth metal hypohalite solution, having a concentration in the range of 2 to 5% is added to a suspension or solution of a sulfide compound of formula (II) to form a reaction mixture, wherein a solution of an alkali or alkali earth metal hydroxide is present in the reaction mixture at least during the oxidation step, is added to a suspension or solution of a sulfide compound of formula (II) whereby the pH of the reaction mixture at least during said oxidation step is in the range of from 9 to 12, and optionally reacting a sulfinyl compound of formula (I) to a pharmaceutically acceptable salt thereof.

2. A process according to claim 1, wherein a compound of formula (II) is reacted with an aqueous hypohalite solution in the presence of a catalyst selected from the group consisting of pyridine, di-isopropyl ethyl amine and N,N-dimethyl amino pyridine.

3. A process according to claim 1, which comprises dissolving or suspending a compound of formula (II) in a solvent selected from the group consisting of water, lower alkyl alcohols, esters, ethers and chlorinated solvents, or a mixture of two or more of these solvents.

4. A process according to claim 3, wherein said solvent is selected from the group consisting of water, methanol, ethanol, isopropanol, di-isopropyl ether, dichloromethane, acetonitrile and ethyl acetate, or a mixture of two or more of these solvents.

5. A process according to claim 1, which is carried out at a temperature in the range of −30 to 50° C.

6. A process according to claim 5, which is carried out at a temperature in the range of 0 to 30° C.

7. A process according to claim 1, wherein said alkali metal or alkali earth metal hypohalite is selected from the group consisting of sodium hypochlorite, sodium hypobromite and calcium hypochlorite.

8. A process according to claim 7, wherein said aqueous hypohalite solution comprises sodium hypochlorite.

9. A process according to claim 1, wherein in formula (I) $R_1$ represents methyl, $R_2$ represents trifluoroethoxy, $R_3$ represents hydrogen and $R_4$ represents hydrogen.

10. A process according to claim 1, wherein in formula (I) $R_1$ represents methyl, $R_2$ represents methoxy, $R_3$ represents methyl and $R_4$ represents methoxy.

11. A process according to claim 1, wherein in formula (I) $R_1$ represents methoxy, $R_2$ represents methoxy, $R_3$ represents hydrogen and $R_4$ represents difluoromethoxy.

12. A process according to claim 1, wherein in formula (I) $R_1$ represents methyl, $R_2$ represents $OCH_2CH_2CH_2OMe$, $R_3$ represents hydrogen and $R_4$ represents hydrogen.

* * * * *

UNITED STATES PATENT AND TRADEMARK OFFICE
CERTIFICATE OF CORRECTION

PATENT NO. : 7,439,367 B2
APPLICATION NO. : 10/542268
DATED : October 21, 2008
INVENTOR(S) : Rajendra Narayanrao Kankan, Dharmaraj Ramachandra Rao and Srinivas L. Pathi It is certified that error appears in the above-identified patent and that said Letters Patent is hereby corrected as shown below:

On the title page, item (75), Inventors, replace "Pathi L. Srinivas" with -- Srinivas Laxminarayan Pathi --

Signed and Sealed this

Fifteenth Day of September, 2009

David J. Kappos
*Director of the United States Patent and Trademark Office*